(12) United States Patent
Matsui et al.

(10) Patent No.: US 7,659,249 B2
(45) Date of Patent: Feb. 9, 2010

(54) MEMBRANE-PERMEABLE NFAT INHIBITORY PEPTIDE

(75) Inventors: Hideki Matsui, 139-11-501, Higashiune, Okayama-shi, Okayama 701-0211 (JP); Masayuki Matsushita, Room 701, 9-45, Saiwai-cho, Kurashiki-shi, Okayama 710-0051 (JP)

(73) Assignees: Japan Science and Technology Agency, Kawaguchi-Shi (JP); Hideki Matsui, Okayama-Shi (JP); Masayuki Matsushita, Kurashiki-Shi (JP)

( * ) Notice: Subject to any disclaimer, the term of this patent is extended or adjusted under 35 U.S.C. 154(b) by 591 days.

(21) Appl. No.: 11/633,529

(22) Filed: Dec. 5, 2006

(65) Prior Publication Data

US 2007/0093427 A1  Apr. 26, 2007

Related U.S. Application Data

(62) Division of application No. 10/504,333, filed as application No. PCT/JP03/02106 on Feb. 26, 2003, now Pat. No. 7,160,863.

(30) Foreign Application Priority Data

Feb. 28, 2002  (JP) ............................... 2002-54912

(51) Int. Cl.
A61K 38/16 (2006.01)
C07K 1/00 (2006.01)
C07K 14/00 (2006.01)

(52) U.S. Cl. .................... 514/12; 530/324; 530/333

(58) Field of Classification Search .................. None
See application file for complete search history.

(56) References Cited

U.S. PATENT DOCUMENTS 5,981,279 A  11/1999  Weiss ......................... 435/375
6,982,082 B1  1/2006  Schreiber et al. ......... 424/93.21

FOREIGN PATENT DOCUMENTS

JP  2002-153288  5/2002
WO  WO 01/43694 A2  6/2001
WO  WO 03/006619 A2  1/2003

OTHER PUBLICATIONS

Aramburu J. et al., "Affinity-Driven Peptide Selection of an NFAT Inhibitor More Selective Than Cyclosporin A", Science, American Association for the Advancement of Science, US, vol. 285, Sep. 24, 1999, pp. 2129-2133, XP 002939935.
Lindgren M. et al., "Cell-Penetrating Peptides", Trends in Pharmacological Sciences, Elsevier, Haywarth, GB, vol. 21, No. 3, Mar. 2000, pp. 99-103, XP002290884.
Noguchi H. et al., "A New Cell-Permeable Peptide Allows Successful Allogeneic Islet Transplantation in Mice", Nature Medicine, vol. 10, No. 3, Mar. 2004, pp. 305-309, XP002351236.
Supplementary European Search Report dated Nov. 9, 2005.
C. Loh, et al., J. Biol. Chem. (1996) 271 (18), pp. 10884-10891.
E. S. Scott, et al., J. Virol. (2001) 75(20), pp. 9955-9965.
M. Matsushita, et al,. J. Neurosci. (2001) 21 (16), pp. 6000-6007.
A. M. Ho, et al., J. Biol Chem. (1994) 269(45), pp. 28181-28186.
T. C. Foster, et al., J. Neurosci. (2001) 21(11), pp. 4066-4073.
Li Hua Jin et al.; "Transduction of Human Catalase Mediated by an HIV-1 TAT Protein Basic Domain and Arginine-Rich Peptides into Mammalian Cells"; Free Radical Biology & Medicine, vol. 31, No. 11, pp. 1509-1519; Dec. 1, 2001.
Donna M. Berry et al.; "Caspase-Dependent Cleavage of the Hematopoietic Specific Adaptor Protein Gads Alters Signalling from the T Cell Receptor"; Oncogene; vol. 20; pp. 1203-1211; Mar. 8, 2001.

*Primary Examiner*—Andrew D Kosar
(74) *Attorney, Agent, or Firm*—Kratz, Quintos & Hanson, LLP

(57) ABSTRACT

The present invention aims to solve the conventional problems by providing a peptide compound, in which when administered to a patient of immunologic disease, cardiac hypertrophy or a disease caused by NFAT activation, the period from administration to actual exhibition of effectiveness is short and there are no side effects or antigenicity. Specifically, the present invention relates to a membrane permeable NFAT inhibitory peptide comprising several consecutive arginines and a NFAT-activity inhibitory peptide sequence; a NFAT activation inhibitory agent comprising the peptide; and a immunosuppressive agent and cardiac hypertrophy suppressive agent, comprising the peptide compound as the active ingredient.

8 Claims, 11 Drawing Sheets

> US 7,659,249 B2

MEMBRANE-PERMEABLE NFAT INHIBITORY PEPTIDE

This is a Divisional of prior application Ser. No. 10/504,333, filed on Aug. 25, 2004 now U.S. Pat. No. 7,160,863, which was a 371 National stage application of PCT/JP03/02106, filed Feb. 26, 2003, these prior applications hereby incorporated by reference.

TECHNICAL FIELD

The present invention relates to a novel peptide compound comprising a signal sequence for biomembrane permeation. Furthermore, the present invention relates to a NFAT activation inhibitory peptide, an immunosuppressive agent and a cardiac hypertrophy suppressive agent comprising several residues of arginine and VIVIT.

BACKGROUND ART

Conventionally, various compounds have been applied as an immunosuppressive agent to immunologic diseases such as rejection after transplant surgery and atopic dermatitis. For example, Cyclosporine A (CysA) and FK 506 are commonly known immunosuppressive agents. However, when administered to animals, these immunosuppressive agents are also known to cause side effects such as loss of renal function, hypertension, decrease of insulin secretion amount and neurotoxicity. Immunosuppressive agents other than CysA and FK 506 have been also been found to cause various side effects and an immunosuppressive agent having fewer side effects is desired.

Currently, besides treatment by the above synthetic compounds, gene therapy, wherein a vector comprising a foreign gene is administered to a human, is attracting attention and studies at a clinical level are being conducted for various diseases. However, the vector used for gene therapy has many problems that need to be solved, such as efficiency of introduction into cells, time required from administration to expression of the protein and side effects when the vector is administered to a human. Also, various peptide preparations have been considered but at present, none are used clinically.

Cardiac hypertrophy refers to the condition of the heart becoming larger than usual due to genetic background or pressure load and may lead to heart failure. However, a cardiac hypertrophy suppressive agent that prevents progression of or promotes involution of cardiac hypertrophy is not commercially available at present. This is because the currently known cardiac hypertrophy suppressive agent has strong side effects and therefore cannot actually be applied to a human. Consequently, medication that prevents or remedies cardiac hypertrophy and does not have problems such as side effects is strongly desired.

DISCLOSURE OF INVENTION

The object of the present invention is to solve the above conventional problems and to provide a peptide compound, in which the time from administration to actually taking effect is short and which does not have side effects or antigenicity. Particularly, the present invention aims to provide a therapeutic agent for immunologic diseases and cardiac hypertrophy. The present invention also relates to a NFAT activation inhibitory agent.

Japanese Patent Application No. 2000-358442 discloses that a peptide comprising 9 to 13 residues of arginine, particularly 11 residues of arginine, is extremely useful as signal sequence for biomembrane permeation. As a result of further studies, it has been found for the first time that an excellent immunosuppressive effect can be obtained when a peptide compound obtained by fusion of 9 to 13 residues of arginine and a peptide that inhibits the activity of Nuclear Factor Activated T cell (NFAT) is used in vivo. Furthermore, when this peptide is administered to a rat suffering from cardiac hypertrophy, the symptoms of cardiac hypertrophy were found to improve considerably and the present invention was achieved.

That is, the present invention relates to a peptide compound comprising 9 to 13 residues of arginine and the amino acid sequence of SEQ ID NO. 1.

The present invention also relates to a NFAT activation inhibitory agent comprising a peptide compound comprising 9 to 13 residues of arginine and the amino acid sequence of SEQ ID NO. 1.

The present invention also relates to an immunosuppressive agent comprising a peptide compound comprising 9 to 13 residues of arginine and the amino acid sequence of SEQ ID NO. 1 as an active ingredient.

The present invention also relates to a cardiac hypertrophy suppressive agent comprising a peptide compound comprising 9 to 13 residues of arginine and the amino acid sequence of SEQ ID NO. 1 as an active ingredient.

BRIEF EXPLANATION OF DRAWINGS

FIG. 7($a$) is a graph showing the insulin secretion amount of cells treated with 11R-VIVIT of the respective concentrations by a relative value to control. FIG. 7($b$) is a graph showing the insulin secretion amount of cells treated with FK 506 of the respective concentrations by a relative value to control. FIG. 7($c$) is a graph showing the insulin secretion amount of cells treated with 11R-VEET of the respective concentrations by a relative value to control.

FIG. 8($a$) is a graph showing the proliferation of cells treated with 11R-VIVIT of the respective concentrations by a relative value to control. FIG. 8($b$) is a graph showing the proliferation of cells treated with FK 506 of the respective concentrations by a relative value to control.

FIG. 9 is a graph showing the results of analyzing the interventricular septum wall thickness and the left ventricle anterior wall thickness of a rat by ultrasonic echo.

FIG. 10(a) is a microscope image showing a section of a normal rat heart. FIG. 10(b) is a microscope image showing a section of an AoB heart. FIG. 10(c) is a microscope image showing a section of a CysA administered AoB heart. FIG. 10(d) is a microscope image showing a section of an 11R-VIVIT administered AoB heart. 3 shows the left ventricle and 4 shows the right ventricle.

FIG. 11 is a graph showing the blood test results of a rat.

BEST MODE FOR CARRING OUT THE INVENTION

Figure 1:
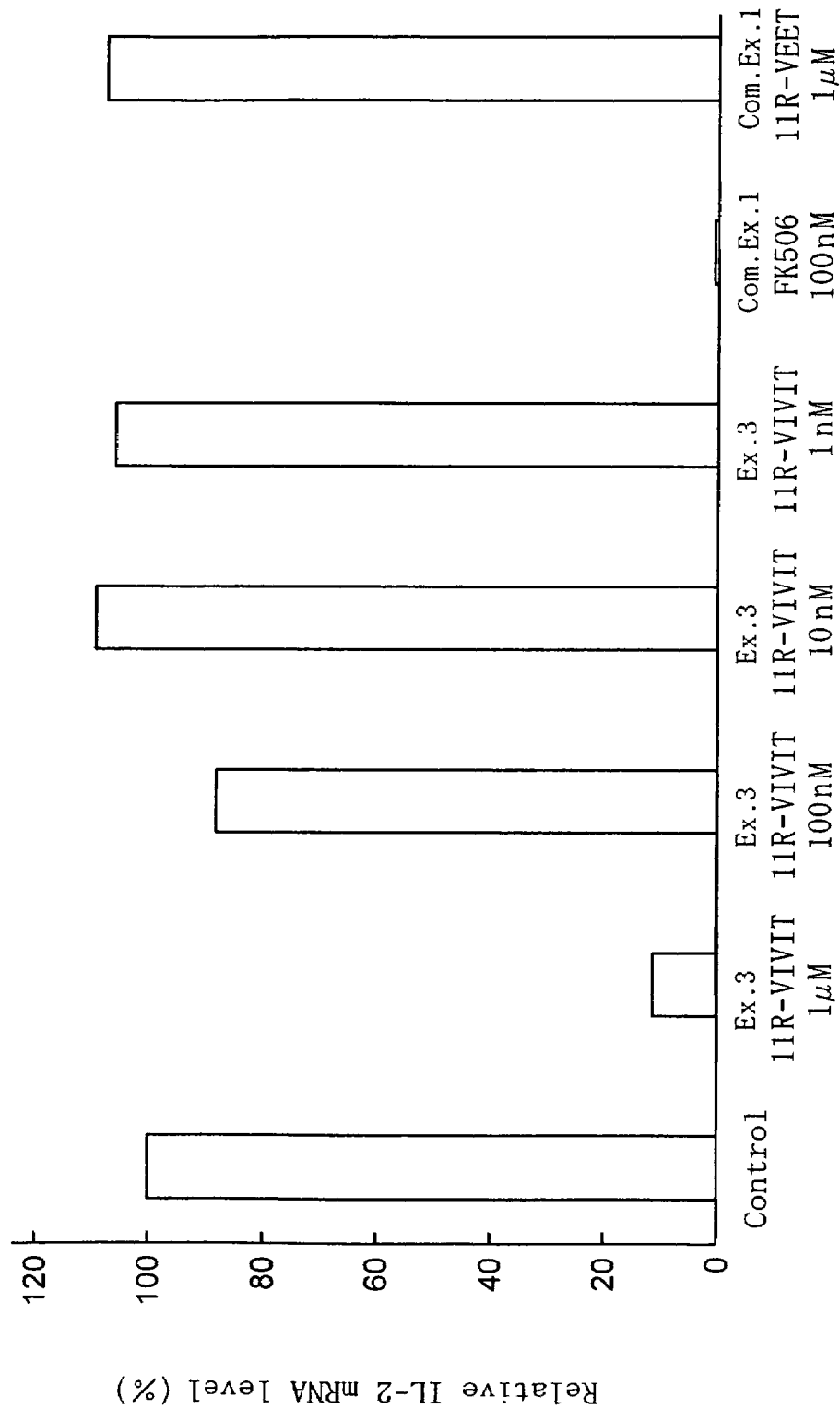
FIG. 1 is a graph showing the transcription amount of IL-2 gene in cells cultured by adding 11R-VIVIT, FK 506 and 11R-VEET in the respective concentrations. The vertical line represents the relative RNA amount of IL-2 gene to GAPDH.

Hereinafter, the peptide compound of the present invention and uses thereof are described in detail.

The peptide compound of the present invention comprises an amino acid sequence having several consecutive arginines and the amino acid sequence of SEQ ID NO. 1.

The number of consecutive arginine residues is preferably 9 to 13, most preferably 11. When the number of consecutive arginine residues is 8 or less or 14 or more, the efficiency of introducing the peptide compound of the present invention into cells tends to become poor.

The peptide compound of the present invention also comprises a NFAT activity inhibitory peptide VIVIT. NFAT is a transcriptional regulatory factor that is activated when dephosphorylated by calcineurin and forms a family including NFAT 1, NFAT 2, NFAT 3 and NFAT 4. VIVIT is a peptide of the amino acid sequence represented by MAGPHPVIVIT-GPHEE (SEQ ID NO. 1). VIVIT selectively inhibits the interaction between proteins that belong to the NFAT family and calcineurin, without influencing the phosphatase activity of calcineurin (Aramburu, J. et al., Science, Vol. 285, pp. 2129 to 2133, 1999). In the amino acid sequence of SEQ ID NO. 1, any amino acid residue can be substituted with a biologically equivalent amino acid residue as long as the amino acid sequence inhibits NFAT and several amino acid residues can be added or deleted as long as the amino acid sequence has biological activity equivalent to VIVIT.

Also, in addition to the above amino sequence comprising several consecutive arginines and the amino acid sequence of SEQ ID NO. 1, the peptide compound of the present invention can have several amino acid residues added, deleted or substituted, as long as the peptide compound has the same biological activity.

Furthermore, the peptide compound of the present invention can contain a marker for confirming introduction into cells. The marker is not particularly limited and for example, fluorescein isothiocyanate (hereinafter referred to as FITC), GFP and rhodamine can be used.

The peptide compound of the present invention can be prepared by the usual artificial synthesis method or by an artificial synthesis machine that is generally commercially available. Also, the peptide compound of the present invention can be prepared using a genetic engineering method. For example, a recombinant vector, in which DNA encoding the peptide sequence comprising a sequence of several consecutive arginines and a sequence of VIVIT is inserted, is prepared and after introducing the recombinant vector in a suitable host cell, the host cell is cultured. Subsequently, by recovering the cultured substance, the peptide compound of the present invention is obtained. After preparing the peptide compound of the present invention, the obtained peptide compound can be purified by a known method. The preparation and purification methods of the peptide compound are common methods in the present field and can be easily conducted by one skilled in the art.

The peptide compound of the present invention can be used as a suppressive agent of NFAT activation. A suppressive agent of NFAT activation can be used as a therapeutic agent for diseases caused by NFAT activation. Examples of diseases caused by NFAT activation are for allergic diseases and cardiac hypertrophy.

The peptide compound of the present invention has the function of inducing immunosuppression and can be used as an immunosuppressive agent for transplant. The immunosuppressive agent of the present invention can also be used as a therapeutic agent for immunologic diseases. Specific examples of immunologic disease are rejection after transplant surgery and atopic dermatitis.

The immunosuppressive agent of the present invention can be administered parenterally, for example, intravenously, hypodermically, intramuscularly, transdermally and intrarectally. Particularly, because decomposition of the peptide compound can be prevented by introducing the peptide compound directly into bloodstream, intravenous or subdermal administration is preferable.

The form of the immunosuppressive agent of the present invention can be determined according to the administration method. Specifically, examples are liquid formulations, such as an aqueous solution and an emulsion, and ointment.

The effective amount of the immunosuppressive agent of the present invention can be determined accordingly in consideration of the administration method and age, weight and medical conditions of the patient and is usually 1 to 10 mg/kg converted to the active ingredient. However, the amount of the peptide compound of the present invention, which is the active ingredient, can be changed and is not limited to the above range.

The immunosuppressive agent of the present invention is not particularly limited as long as it comprises the peptide compound of the present invention as the active ingredient and other components that are usually used in this technical field can be added, such as a suitable pharmaceutical excipient, a suitable carrier, a solvent, a gel forming agent, an antioxidant, a diluent, an isotonizing agent and a pH stabilizer. These additives can usually be selected accordingly by one skilled in the art.

The peptide compound of the present invention is effective as a cardiac hypertrophy suppressive agent. The cardiac hypertrophy suppressive agent of the present invention can be administered parenterally, for example intravenously, hypodermically, intramuscularly, transdermally or intrarectally. Particularly, because introducing the peptide compound directly into bloodstream is important for of preventing decomposition of the peptide compound, intravenous administration is preferable.

The form of the cardiac hypertrophy suppressive agent of the present invention can be determined according to the administration method. Specifically, examples are liquid formulations, such as an aqueous solution or an emulsion, and ointment.

The dosage of the cardiac hypertrophy suppressant of the present invention can be determined accordingly in consideration of the administration method and age, weight and medical conditions of the patient and is usually 0.1 to 2 mg/kg converted to the active ingredient. However, the amount of the peptide compound of the present invention, which is the active ingredient, can be changed and is not limited to the above range.

The cardiac hypertrophy suppressive agent of the present invention is not particularly limited as long as it contains the peptide compound of the present invention as the active ingredient and other components that are usually used in this technical field can be added, such as a suitable pharmaceutical excipient, a suitable carrier, a solvent, a gel forming agent, an antioxidant, a diluent, an isotonizing agent and a pH stabilizer. These additives can usually be selected accordingly by one skilled in the art.

Hereinafter, the peptide compound of the present invention is described in more detail by means of Examples, but the present invention is not limited thereto as long as the purpose and scope of the present invention are not deviated from.

EXAMPLE 1

A peptide compound comprising 11 consecutive arginine residues, VIVIT and FITC was artificially synthesized (preparation commissioned to Sigma Genosis Japan, Inc.) and the peptide was purified by reversed-phase HPLC. Hereinafter, a peptide comprising 11 consecutive arginine residues and VIVIT to which 3 glycine residues are added is referred to as 11R-VIVIT. The peptide sequence of 11R-VIVIT is shown in SEQ ID NO. 2. FITC is added to the amino terminal of 11R-VIVIT.

EXAMPLE 2

A six-week old C3H/HeN mouse H-2k (available from CLEA Japan, Inc.) was subjected to intraperitoneal injection with 0.5 ml of a Ringer solution, in which 10 mg/kg of the peptide compound comprising 11R-VIVIT and FITC prepared in Example 1 was dissolved, as the injection. 6 hours after injection, the spleen, the lymph node, the liver, the kidney and the heart were removed from each mouse and each were frozen at −80° C. in 3 ml of Histo Prep® (available from Fisher Scientific International, Inc.). Then, sections of 10 to 50 μm were prepared on a cryostat and analyzed by a Zeiss microscope (made by Carl Zeiss, Inc.). As control, sections of an untreated C3H/HeN mouse were used.

As a result of analysis, in each of the sections of the spleen, the lymph node, the liver, the kidney and the heart derived from the mouse to which the complex peptide was administered, fluorescence of FITC was observed. On the other hand, in the control section, fluorescence of FITC was not observed. This indicates that by intraperitoneal administration, 11R-VIVIT is introduced into at least the cells of the spleen, the lymph node, the liver, the kidney and the heart.

EXAMPLE 3

The dose dependant effect of 11R-VIVIT to transcription of IL-2 gene was studied.

Using 1 ml of 10% fetal bovine serum-containing RPMI (available from Invitrogen BV) containing 1 nM, 10 nM, 100 nM or 1 μM of 11R-VIVIT, $1 \times 10^5$ Jurkat cells were cultured for 1 hour in a carbon dioxide culture device (made by Sanyo Denki Co., Ltd.) set to 37° C. and carbon dioxide concentration of 5%. Subsequently, 100 μl of RPMI containing 2 μM of phorbol 12-myristate 13-acetate (PMA) (available from Sigma-Aldrich Co.) and 40 μM of ionomycin (available from Sigma-Aldrich Co.) was added and culture was continued for 12 more hours. Then, the cells were recovered and using the obtained cells, the transcription amount of IL-2 gene was measured by the following real-time quantitative RT-PCR. In real-time quantitative RT-PCR, GAPDH, which is known as a housekeeping gene, was used as the inner standard substance. Also, real-time quantitative RT-PCR was conducted in the same manner, using Jurkat cells cultured in a medium without 11R-VIVIT as control cells.

RNeasy Mini Kit (available from QIAGEN K.K.) was used according to protocol and total RNA was extracted from the cells. Using the obtained total RNA, reverse transcription reaction was conducted by incubation at 22° C. for 10 minutes and then at 42° C. for 20 minutes.

Thereafter, using Light Cycler-Fast Start DNA Master SYBR Green I Kit (available from Roche Molecular Biochemicals), 20 μl of a mixed reaction solution (1/10 of the amount of the transcription product, 4 mM of $MgCl_2$, 4 kinds of primers: 0.5 μM respectively, 2 μl of 10×Light Cycler-Fast Start DNA Master SYBR Green I) was prepared for amplification reaction. As the primer for human IL-2, the primer included in Competitive Quantitative RT-PCR Kit (available from Funakoshi Co., Ltd.) was used. As the primer for GAPDH, 5'-CTGACCAGGGTCCTATTCCA-3' (SEQ ID NO. 5) and 5'-TGGTTATCCCAAGCAAGAGG-3' (SEQ ID NO. 6) (both available from Gene Set) were used. The amplification reaction was conducted by incubation at 95° C. for 10 minutes and then 60 cycles of incubation at 94° C. for 15 seconds, 57° C. for 5 seconds and 72° C. for 10 seconds. Subsequently, the temperature was raised to 95° C. at a rate of 0.2° C./second. For dissociation curve analysis, Light Cycler Software (available from Roche Molecular Biochemicals) was used. The relative RNA amount to GAPDH found by analysis is shown in FIG. 1 (n=3).

11R-VIVIT suppressed the transcription of IL-2 gene to 12% of the case wherein treatment was not conducted. IL-2 gene is a gene, in which transcription is promoted, when T cells are activated by allergies and rejection. Consequently, the results indicate that 11R-VIVIT can suppress T cell activation.

COMPARATIVE EXAMPLE 1

A peptide compound comprising 11 consecutive arginine residues and VEET to which 3 glycine residues are added (hereinafter referred to as 11R-VEET) was artificially synthesized and purified in the same manner as in Example 1. VEET is a peptide of the amino acid sequence represented by MAGPPHIVEETGPHVI (SEQ ID NO. 3). The peptide sequence of 11R-VEET is shown in SEQ ID NO.4. Hereinafter, 11R-VEET is used as negative control of 11R-VIVIT.

Jurkat cells were cultured and RT-PCR was conducted using the obtained cells in the same manner as in Example 3, except that a medium containing 100 nM of FK 506 (available from Fujisawa Pharmaceutical Co., Ltd.) or 1 μM of 11R-VEET, instead of 11R-VIVIT, was used. The results are shown in FIG. 1.

11R-VEET did not affect the transcription level of IL-2 gene.

EXAMPLE 4

The half-life of 11R-VIVIT in T cells was studied based on inhibitory activity to IL-2 transcription.

Using 1 ml of 10% fetal bovine serum-containing RPMI containing 1 μM of 11R-VIVIT, $1\times10^5$ Jurkat cells were cultured for 1 hour in a carbon dioxide culture device set to 37° C. and carbon dioxide concentration of 5%. Subsequently, 100 μl of RPMI containing 2 μM of PMA and 40 μM of ionomycin was added and culture was conducted further for 12 hours, 17 hours, 23 hours, 35 hours or 59 hours. As control cells, Jurkat cells, cultured in the same manner as above for 1 hour in 10% fetal bovine serum-containing RPMI without 11R-VIVIT and then cultured further for 12 hours, 17 hours, 23 hours, 35 hours or 59 hours after adding 100 μl of RPMI containing 2 μM of PMA and 40 μM of ionomycin, were used.

Figure 2:
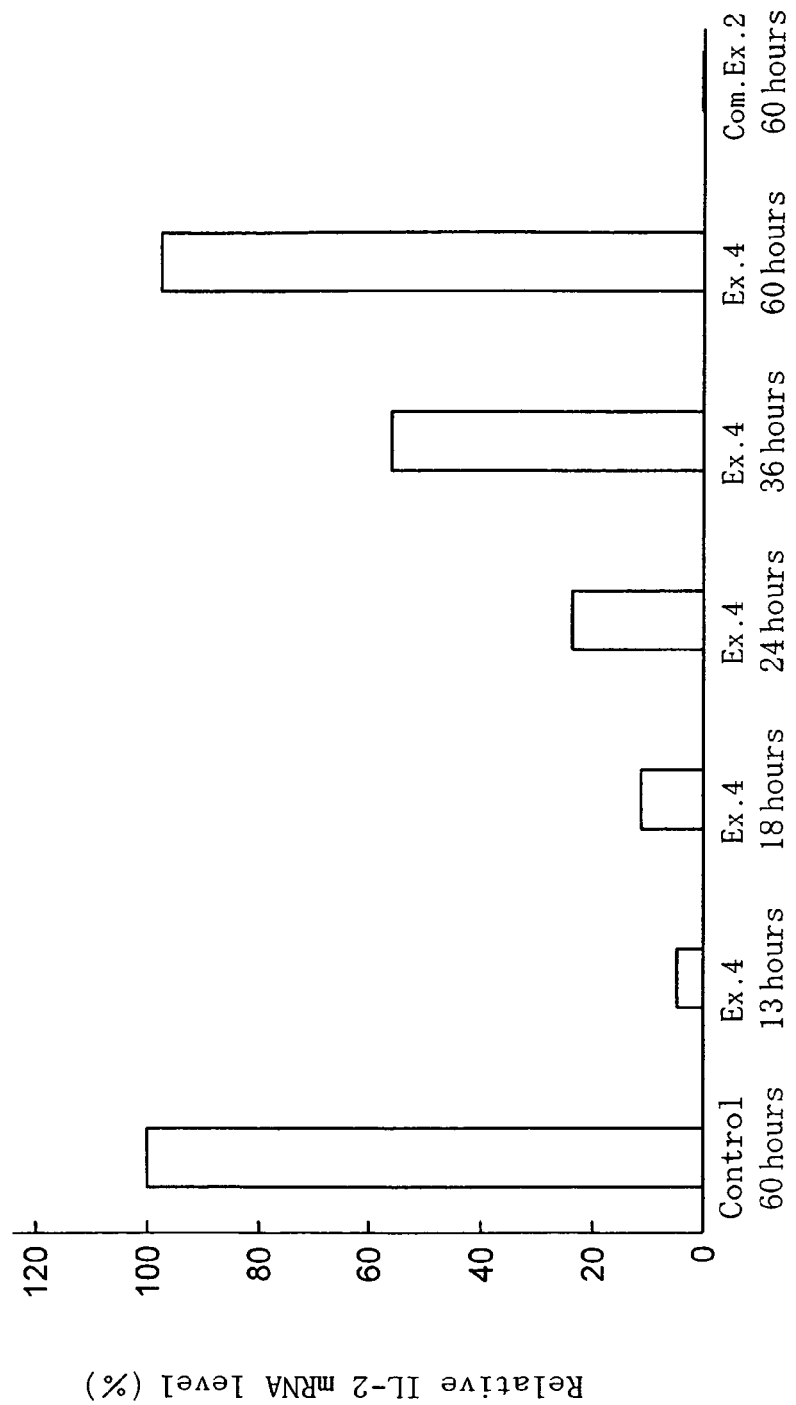
FIG. 2 is a graph showing the transcription amount of IL-2 gene in Jurkat cells cultured for 60 hours in only a RPMI medium containing 10% fetal bovine serum, Jurkat cells cultured for 13 hours, 18 hours, 24 hours, 36 hours and 60 hours after adding 11R-VIVIT and Jurkat cells cultured for 60 hours after adding FK 506. The vertical line represents the relative RNA amount of IL-2 gene to GAPDH.

Subsequently, the relative RNA amount to GAPDH was measured by conducting RT-PCR and real-time quantitative RT-PCR and analysis in the same manner as in Example 3, except that the respective obtained cells were used as samples. The results are shown in FIG. 2 (n=3). The time shown in FIG. 2 refers to the total culture time.

The half-life of 11R-VIVIT was approximately 30 hours. 60 hours after 11R-VIVIT was added, the IL-2 transcription inhibitory activity thereof could not be observed.

COMPARATIVE EXAMPLE 2

Using 1 ml of 10% fetal bovine serum-containing RPMI containing 1 μM of FK 506, $1\times10^5$ Jurkat cells were cultured for 1 hour in a carbon dioxide culture device set to 37° C. and carbon dioxide concentration of 5%. Subsequently, 100 μl of RPMI containing 2 μM of PMA and 40 μM of ionomycin was added and culture was conducted further for 12 hours, 17 hours, 23 hours, 35 hours or 59 hours. Thereafter, RT-PCR and real-time quantitative RT-PCR were conducted in the same manner as in Example 3, except that the obtained culture cells were used. The relative IL-2 mRNA level 60 hours after adding FK 506 is shown in FIG. 2.

FK 506 was not metabolized even after 60 hours and strongly suppressed transcription of IL-2.

EXAMPLE 5

The effect of 11R-VIVIT to activation and proliferation of T cells was studied by mixed lymphocyte test.

Spleen cells were retrieved from a 6 to 8 week old C3H/HeN mouse and a 6 to 8 week old BALB/c mouse H-2d (available from Shimizu Laboratory Supplies Co., Ltd.). The BALB/c spleen cells were treated with mitomycin C (available from Kyowa Hakko Kogyo Co., Ltd.) and used as stimulating cells.

RPMI containing 1 pM, 1 nM or 1 μM of 11R-VIVIT was added to a flat-bottomed 96-well plate (available from Iwaki & Co., Ltd.). Subsequently, $5\times10^5$ of mixed cells obtained by mixing the above stimulating cells and the spleen cells derived from a C3H/HeN mouse in a ratio of 1:5 were added in each well and cultured for 90 hours in a carbon dioxide culture device set to 37° C. and carbon dioxide concentration of 5%. As control, the mixed cells were added to wells containing only a medium and cultured in the same manner.

Figure 3:
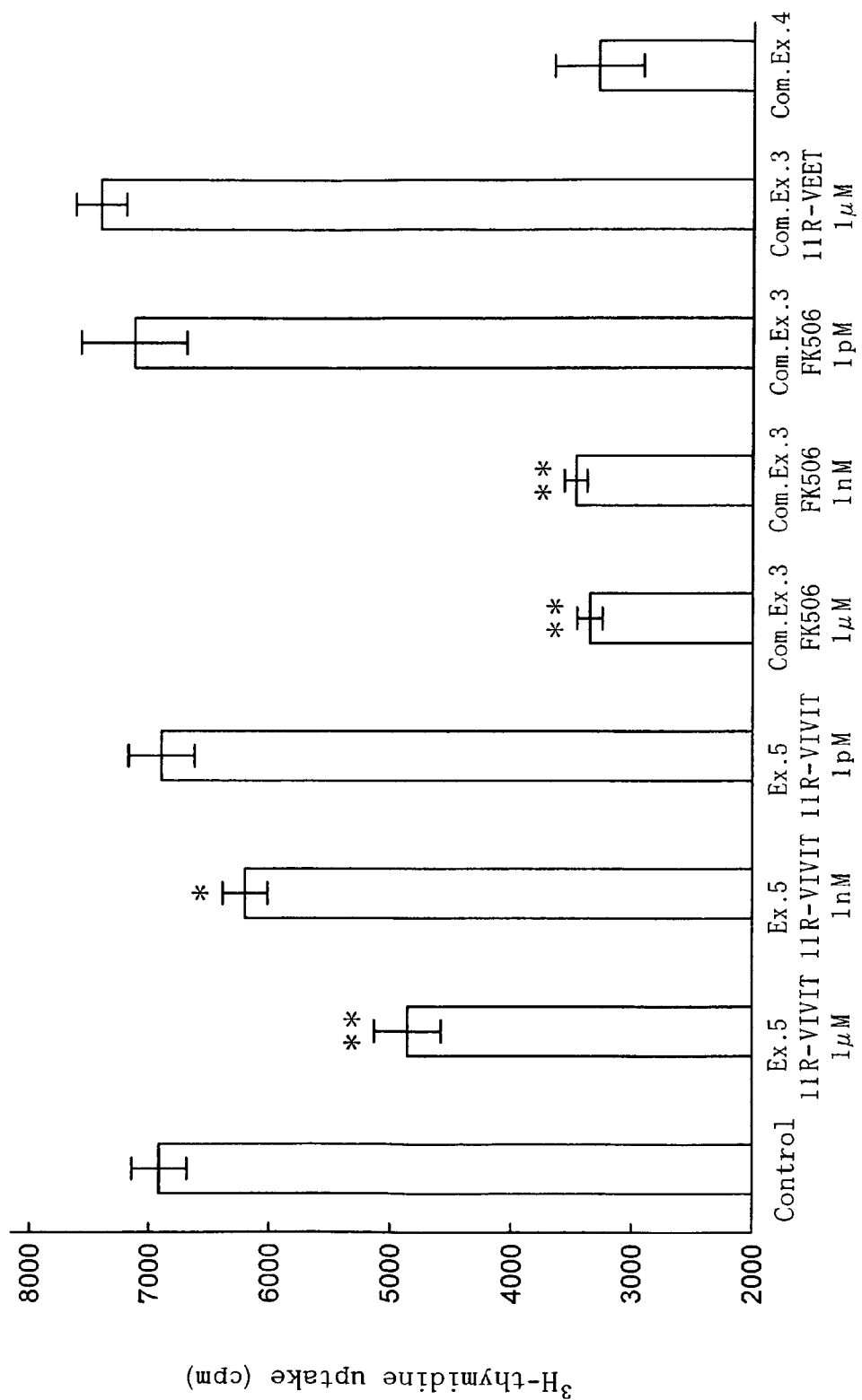
FIG. 3 is a graph showing the radioactivity of [$^3$H]TdR incorporated into cells in a mixed lymphocyte test.

Then, $^3$H-methyl-thymidine (hereinafter referred to as [$^3$H]TdR, available from Amersham Pharmacia Biotech K.K.) of 0.5 μCi/well was added and culture was conducted for 6 hours. Thereafter, the cells were placed on filter paper having a diameter of 1 cm and the radioactivity of [$^3$H]TdR incorporated into the cells was measured by a beta counter (made by Beckman Coulter K.K.). The results are shown in FIG. 3.

1 μM of 11R-VIVIT suppressed proliferation of lymphocytes by 43% based on control. In FIG. 3, * indicates that P<0.05 in comparison to control and ** indicates that P<0.001.

COMPARATIVE EXAMPLE 3

Mixed cells were cultured, [$^3$H]TdR was added and the radioactivity of [$^3$H]TdR incorporated into the cells was measured by a beta counter in the same manner as in Example 5, except that RPMI containing 1 pM, 1 nM or 1 μM of FK 506 or 1 μM of 11R-VEET instead of 11R-VIVIT was used. The results are shown in FIG. 3.

Proliferation of lymphocytes was not affected by 1 μM of 11R-VEET.

COMPARATIVE EXAMPLE 4

Cells were cultured, [$^3$H]TdR was added and the radioactivity of [$^3$H]TdR incorporated into the cells was measured by a beta counter in the same manner as in Example 5, except that RPMI that does not contain 11R-VIVIT was used as the medium and only spleen cells derived from a C3H/HeN mouse was used instead of mixed cells. The results are shown in FIG. 3.

EXAMPLE 6

0.5 ml of a Ringer solution in which 10 mg/kg of 11R-VIVIT was dissolved was used as the injection and the effect of 11R-VIVIT to activation and proliferation of T cells in vivo was studied.

The above injection was injected intraperitoneally to a 6 week old C3H/Hen mouse once a day for 2 days.

6 hours after the second injection, the spleen was surgically removed. The obtained spleen cells ($1\times10^4$ cells) were added to a flat-bottomed 96-well plate together with spleen cells ($1\times10^5$ cells) of a BALB/c mouse treated with mitomycin C and cultured for 90 hours in a carbon dioxide culture device set to 37° C. and carbon dioxide concentration of 5%. RPMI was used as the medium. For control, the mixed cells were added to wells containing only medium and cultured in the same manner.

Figure 4:
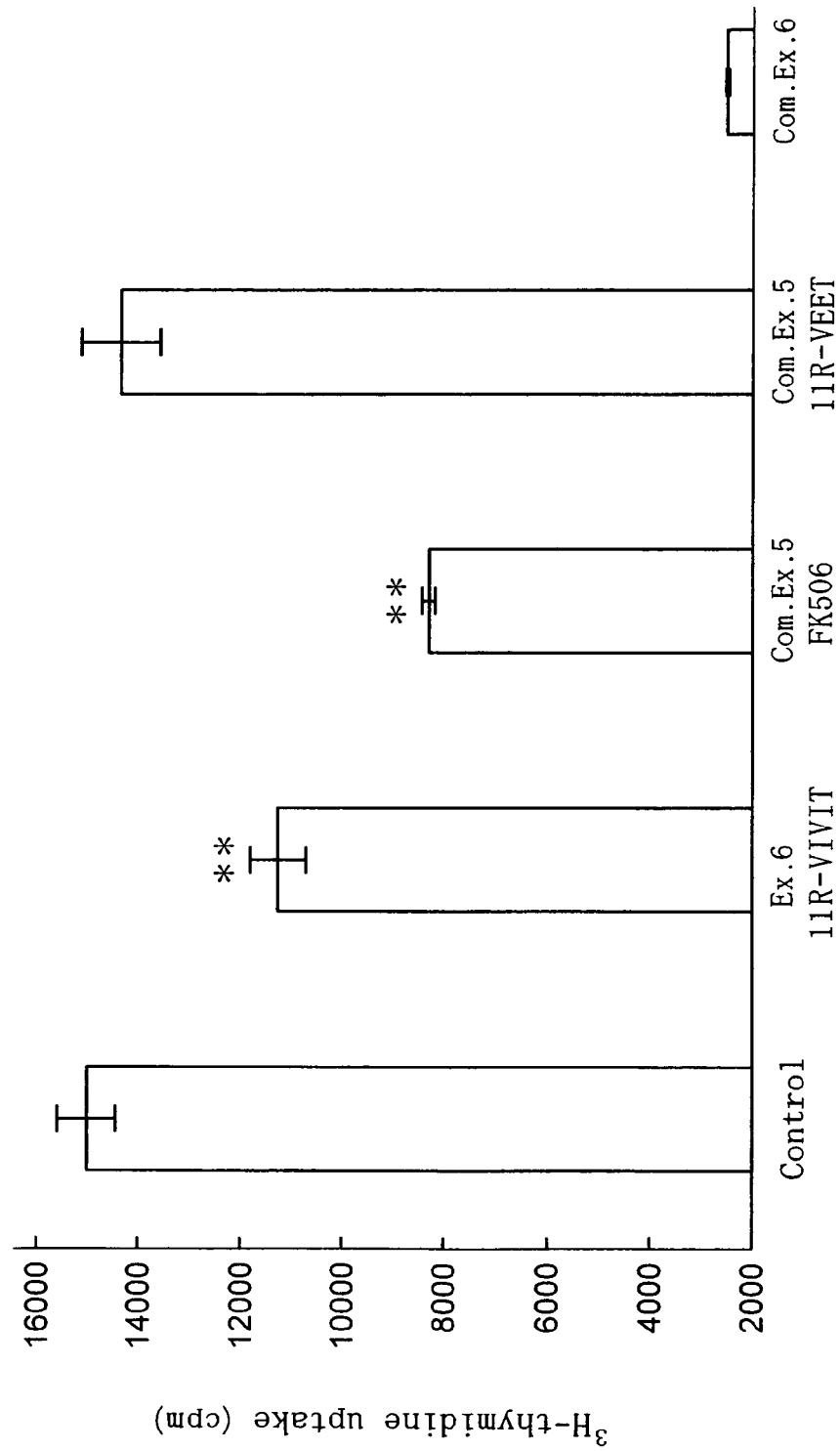
FIG. 4 is a graph showing the radioactivity of [$^3$H]TdR incorporated into cells in a mixed lymphocyte test using cells obtained from a mouse to which 11R-VIVIT, FK 506 and 11R-VEET are administered.

Then, [$^3$H]TdR of 0.5 μCi/well was added and culture was conducted for 6 hours. Thereafter, the cells were placed on filter paper having a diameter of 1 cm and the radioactivity of [$^3$H]TdR incorporated into the cells was measured by a beta counter. The results are shown in FIG. 4. In FIG. 4, ** indicates that P<0.001 in comparison to control.

10 mg/kg of 11R-VIVIT exhibited a suppression effect of 30% to control in vivo.

COMPARATIVE EXAMPLE 5

A C3H/HeN mouse was subjected to intraperitoneal injection, spleen cells were retrieved and cultured, [$^3$H]TdR was added and the radioactivity of [$^3$H]TdR incorporated into the cells was measured by a beta counter in the same manner as in Example 6, except that 1 mg/kg of FK 506 or 10 mg/kg of 11R-VEET was used, instead of 11R-VIVIT. The results are shown in FIG. 4.

Proliferation of lymphocytes was not affected by 1 µM of 11R-VEET.

COMPARATIVE EXAMPLE 6

Cells were cultured, [$^3$H]TdR was added and the radioactivity of [$^3$H]TdR incorporated into the cells was measured by a beta counter in the same manner as in Example 6, except that RPMI without 11R-VIVIT was used as the medium and spleen cells derived from a C3H/HeN mouse were used instead of mixed cell. The results are shown in FIG. 4.

EXAMPLE 7

0.5 ml of a Ringer solution in which 10 mg/kg of 11R-VIVIT was dissolved was used as the injection and the effect of 11R-VIVIT in beta cell transplant was studied. For the transplant, a 6 week old BALB/c mouse was used as the donor and a 6 week old C3H/HeN mouse was used as the recipient.

A diabetic model mouse was prepared by intraperitoneally injecting 220 mg/kg of streptozocin (available from Sigma-Aldrich Japan K.K.) to a C3H/HeN mouse. 6 days after the streptozocin injection, the mouse in which the glucose level exceeded 350 mg/dl was determined as being hyperglycemic.

Meanwhile, the spleen of the BALB/c mouse was taken out and after subjecting to discontinuous Ficoll density gradient centrifugation, beta cells were isolated by normal collagenase digestion.

Figure 5:
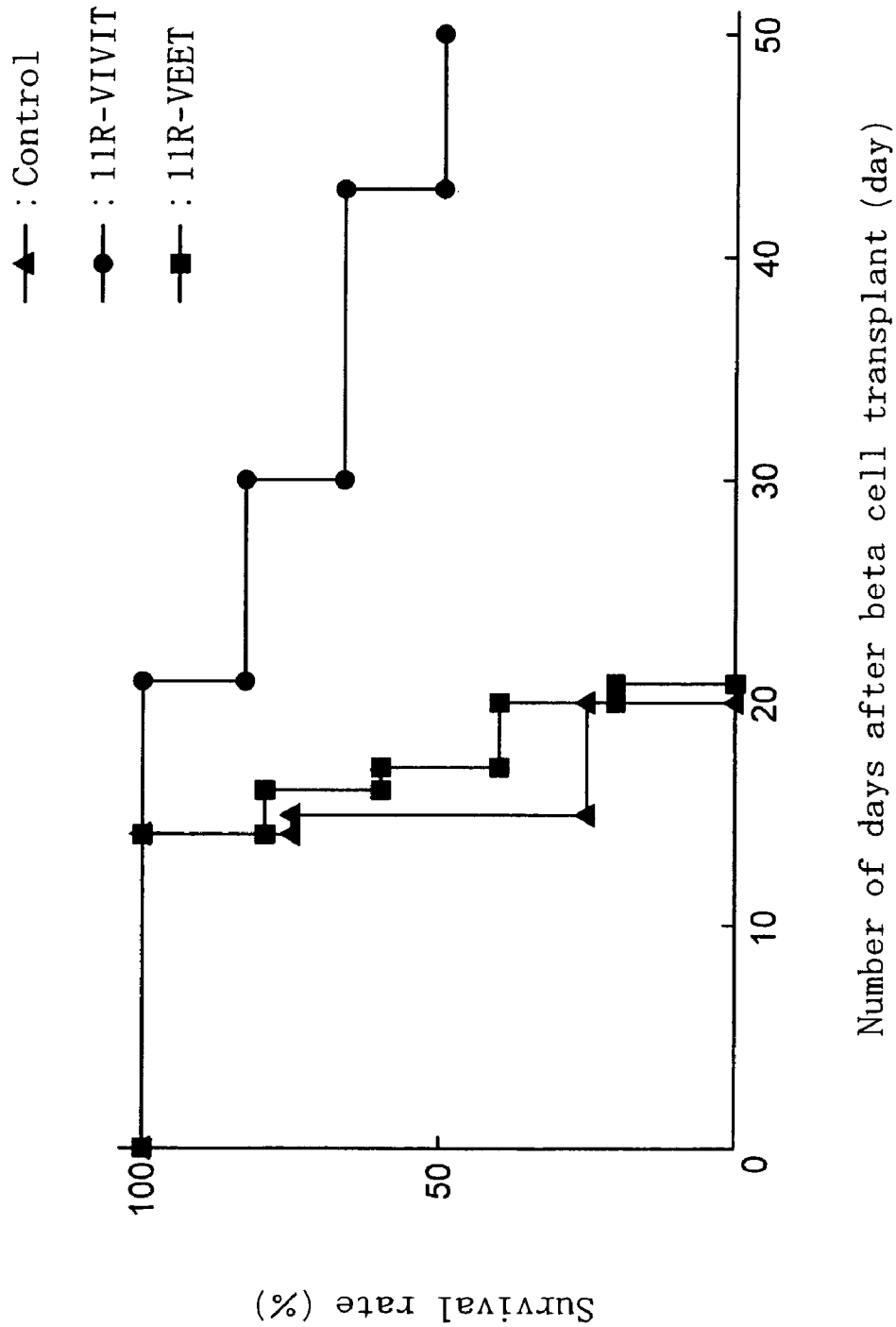
FIG. 5 is a graph evaluating the survival rate of transplanted beta cells by Kaplan-Meier.

About 500 of the isolated beta cells were transplanted under the capusula of the left kidney of the above diabetic model mouse. After the transplant, 10 mg/kg of 11R-VIVIT was intraperitoneally injected to the mouse once a day (n=6). For control, physiologic saline that does not contain 11R-VIVIT was injected in the mouse to which the beta cells were transplanted (n=4). The glycemia was measured and when the level thereof exceeded 200 mg/dl for 2 consecutive days, transplant rejection was considered to have occurred. The results evaluated by Kaplan-Meier are shown in FIG. 5.

By administering 11R-VIVIT, the survival rate increased significantly compared to control (P<0.005).

COMPARATIVE EXAMPLE 7

The effect of 11R-VEET to beta cell transplant was studied in the same manner as in Example 7, except that 10 mg/kg of 11R-VEET was used instead of 11R-VIVIT. The results are shown in FIG. 5.

As in the case of control, 11R-VEET did not affect the survival of the transplant.

EXAMPLE 8

Using the mouse to which 11R-VIVIT was administered in Example 1, the function of the transplanted beta cells were studied.

50 days after the beta cell transplant, the kidney was surgically removed. Then, using frozen mitochrome (available from Carl Zeiss, Inc.), a 30 µm kidney section was prepared. The obtained section was subjected to immunostaining using a polyclonal antibody against insulin (available from Santa Cruz Biotechnology, Inc.), avidin and biotin peroxidase method (available from Vector Laboratories, Inc.).

Figure 6:
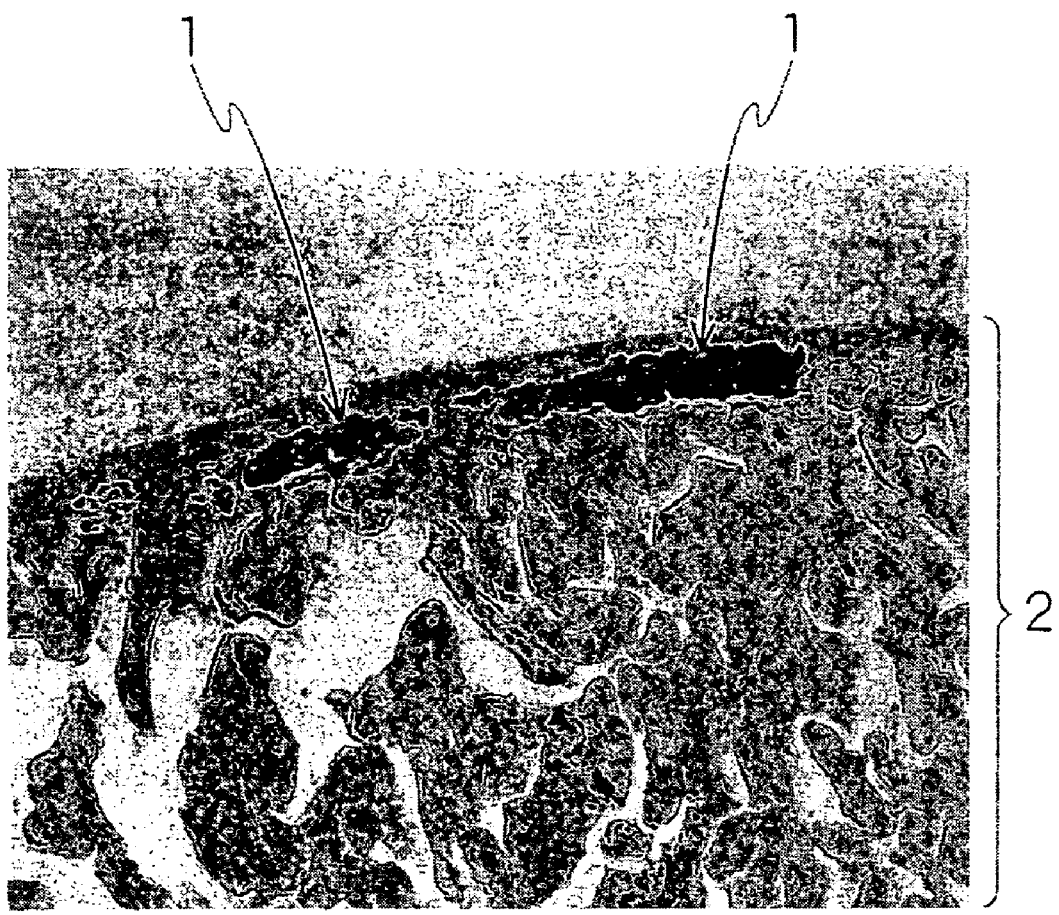
FIG. 6 is a microscope image showing the results of immunostaining transplanted beta cells. 1 shows beta cells of a BALB/c mouse. 2 shows the kidney of a diabetic model mouse.

The results of immunostaining are shown in FIG. 6. In FIG. 6, 1 represents the transplanted beta cells and 2 represents the kidney of the recipient. The transplanted cells were confirmed to produce insulin, as the transplanted beta cells were stained by the anti-insulin antibody.

EXAMPLE 9

The effect of 11R-VIVIT to insulin secretion of βTC6 cells was studied. βTC6 cells are cell lines of islets of Langerhans, which secrete insulin by glucose response.

βTC6 cells (available from American Type Culture Collection, CRL-11506) were added to a 96 well plate (5×10$^4$ cell/well) and cultured for 96 hours using 1 ml of 10% fetal bovine serum-containing RPMI containing 10, 100, 1000 or 10000 nM of 11R-VIVIT in a carbon dioxide culture device set to 37° C. and carbon dioxide concentration of 5%. The medium was replaced with a fresh medium containing 11R-VIVIT every 24 hours. After 96 hours, the medium was replaced with a fresh medium. Culture was conducted for 1 more hour and the culture supernatant was collected. For control, βTC6 cells were cultured in the same manner, except that a medium without 11R-VIVIT was used.

Figure 7A:
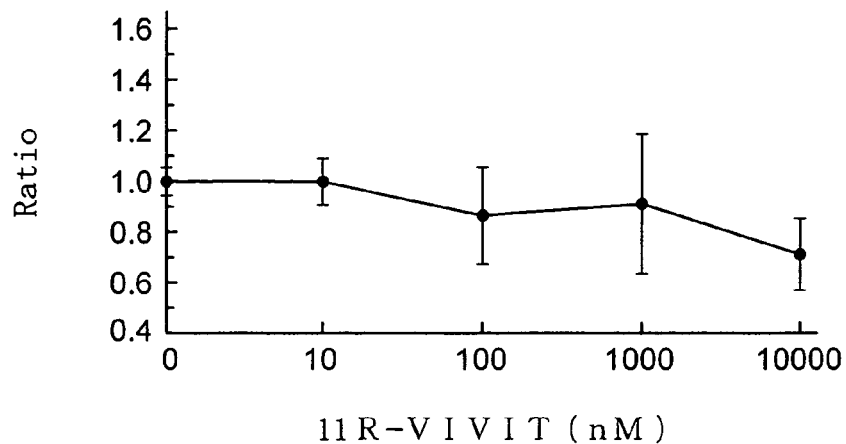
FIG. 7 is a graph showing the insulin secretion amount of cells subjected to the respective treatments by a relative value to control.

Subsequently, using the collected supernatant, the secreted insulin was analyzed using Mouse Insulin ELISA (TMB) Kit (available from Shibayagi Co., Ltd.) according to protocol. FIG. 7(a) shows the amount of insulin secretion of cells treated with 11R-VIVIT by a relative value to control.

The insulin secretion amount of βTC6 cells was almost the same as control when the amount of 11R-VIVIT was within the range of 0 to 1 µM. However, when the amount of 11R-VIVIT was 10 µM, the insulin secretion amount was 71% of control (P=0.042).

Figure 7B:
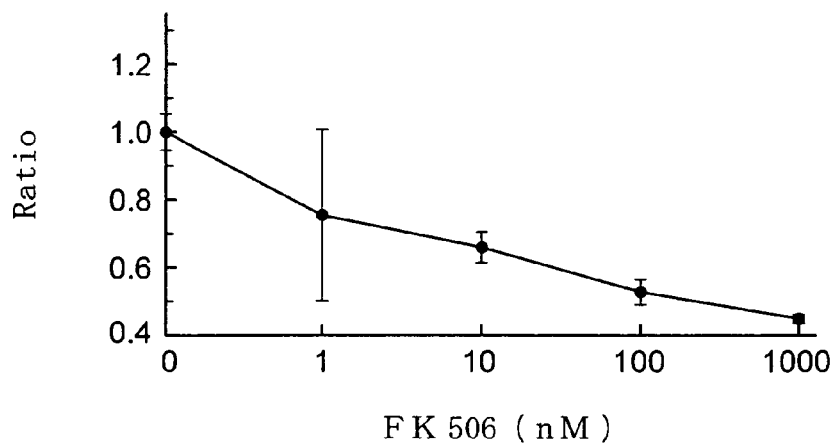
Figure 7C:
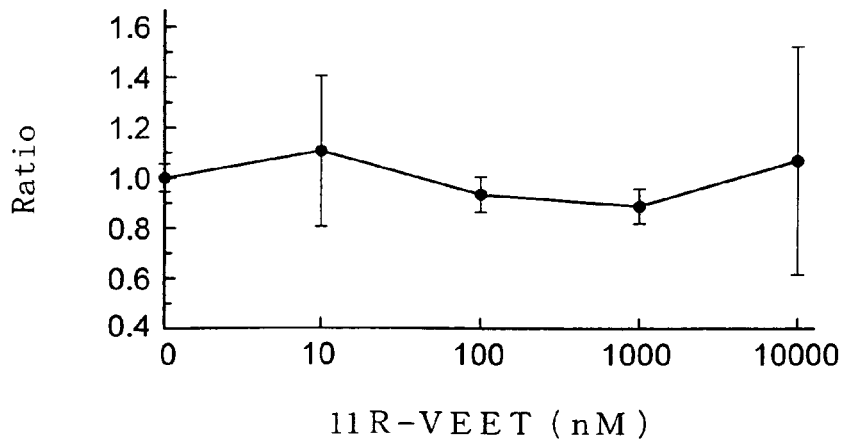

COMPARATIVE EXAMPLE 8

βTC6 cells were cultured and the effect to insulin secretion of βTC6 cells was studied in the same manner as in Example 9, except that a complete medium containing 1, 10, 100 or 1000 nM of FK 506 or 10, 100, 1000 or 10000 nM of 11R-VEET, instead of 11R-VIVIT, was used. The results are shown in FIGS. 7(b) and 7(c).

The insulin secretion amount of βTC6 cells was significantly decreased by FK 506 and unaffected by 11R-VEET.

EXAMPLE 10

Figure 8A:
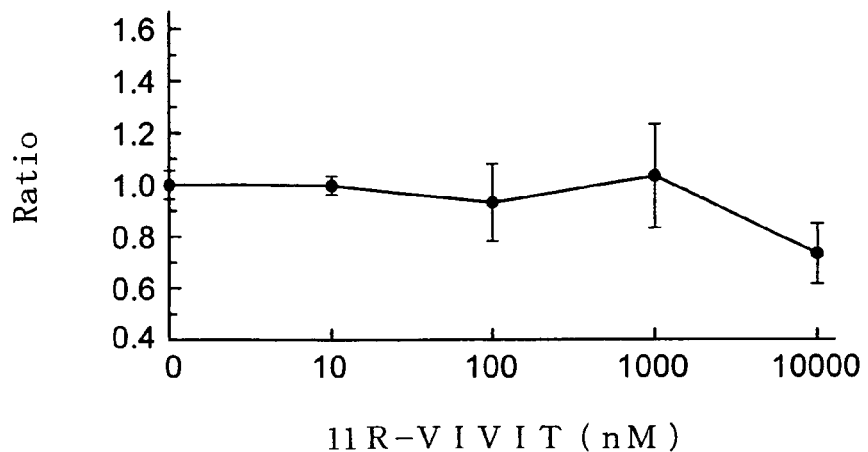
FIG. 8 is a graph showing the proliferation of cells subjected to the respective treatments by a relative value to control.
FIG. 8(c) is a graph showing the proliferation of cells treated with 11R-VEET of the respective concentrations by a relative value to control.

The effect of 11R-VIVIT to proliferation of βTC6 cells was studied.

βTC6 cells were added to a 96 well plate (5×10$^4$ cell/well) and cultured for 88 hours using a complete medium containing 10, 100, 1000 or 10000 nM of 11R-VIVIT in a carbon dioxide culture device set to 37° C. and carbon dioxide concentration of 5%. The medium was replaced with a fresh medium containing 11R-VIVIT every 24 hours. Subsequently, [$^3$H]TdR of 1 µCi/well was added and culture was conducted for 8 more hours. For control, βTC6 cells were cultured in the same manner except that a medium without 11R-VIVIT was used. Thereafter, the cells were placed on filter paper having a diameter of 1 cm and the radioactivity of [$^3$H]TdR incorporated into the cells was measured by a beta counter. FIG. 8(a) shows proliferation of cells treated with 11R-VIVIT by a relative value to control.

Proliferation of βTC6 cells was almost the same as control when the amount of 11R-VIVIT was within the range of 0 to 1 µM. When the amount of 11R-VIVIT was 10 µM, proliferation was 73% of control (P=0.075).

Figure 8B:
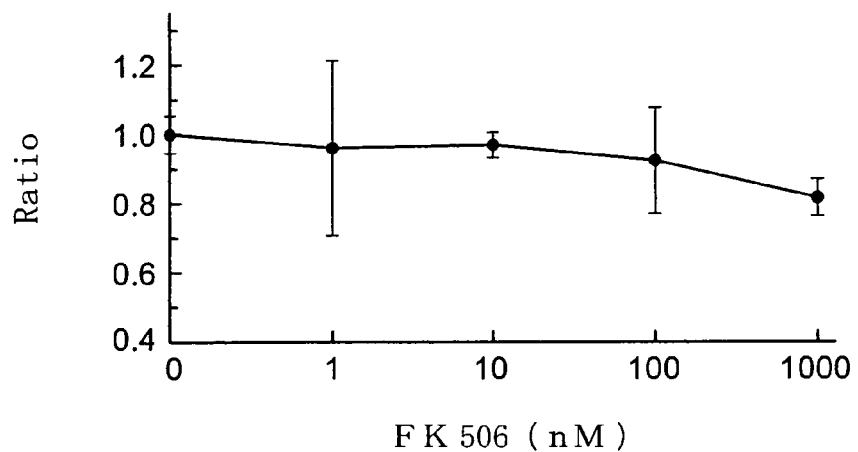
Figure 8C:
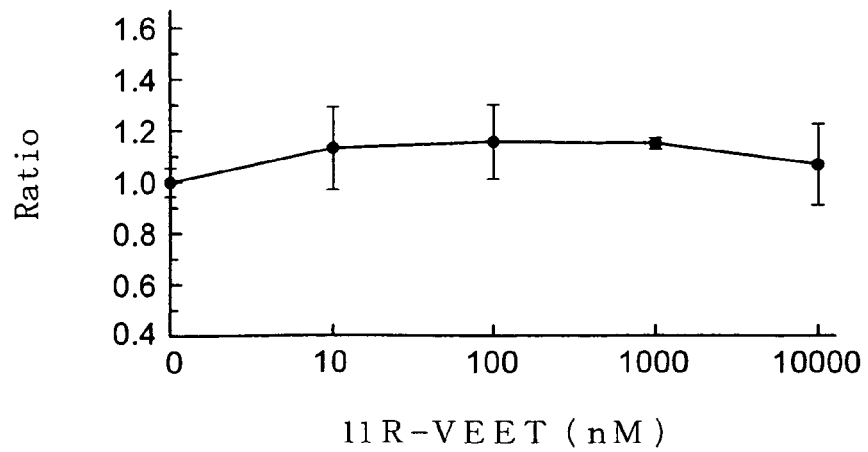

COMPARATIVE EXAMPLE 9

βTC6 cells were cultured and the effect to proliferation of βTC6 cells was studied in the same manner as in Example 10, except that a complete medium containing 1, 10, 100 or 1000 nM of FK 506 or 10, 100, 1000 or 10000 nM of 11R-VEET, instead of 11R-VIVIT, was used. The results are shown in FIGS. 8(b) and 8(c).

FK 506 and 11R-VEET did not exhibit an inhibitory effect to proliferation of βTC6 cells.

EXAMPLE 11

The effect of 11R-VIVIT to cardiac hypertrophy was studied.

A cardiac hypertrophy model rat was hypodermically injected every other day with 0.5 ml of Ringer solution in which 1.5 mg/kg of 11R-VIVIT was dissolved (n=6). The cardiac hypertrophy model rat was prepared by ligating the aorta of a 7 week old male Wistar rat having weight of 200 to 250 g (available from Shimizu Laboratory Supplies Co., Ltd.) and applying pressure load. In the present specification, the cardiac hypertrophy model rat is referred to as AoB.

Subsequently, the heart of the rat was evaluated by the following methods after 0, 1, 2, 3, 4, and 5 weeks. As control, a normal rat to which 11R-VIVIT was not administered was used.

Control and 11R-VIVIT administered AoB were subjected to ultrasonic echo test (ULC) and preparation of tissue specimen and blood test were conducted in the following manner.

Figure 9A:
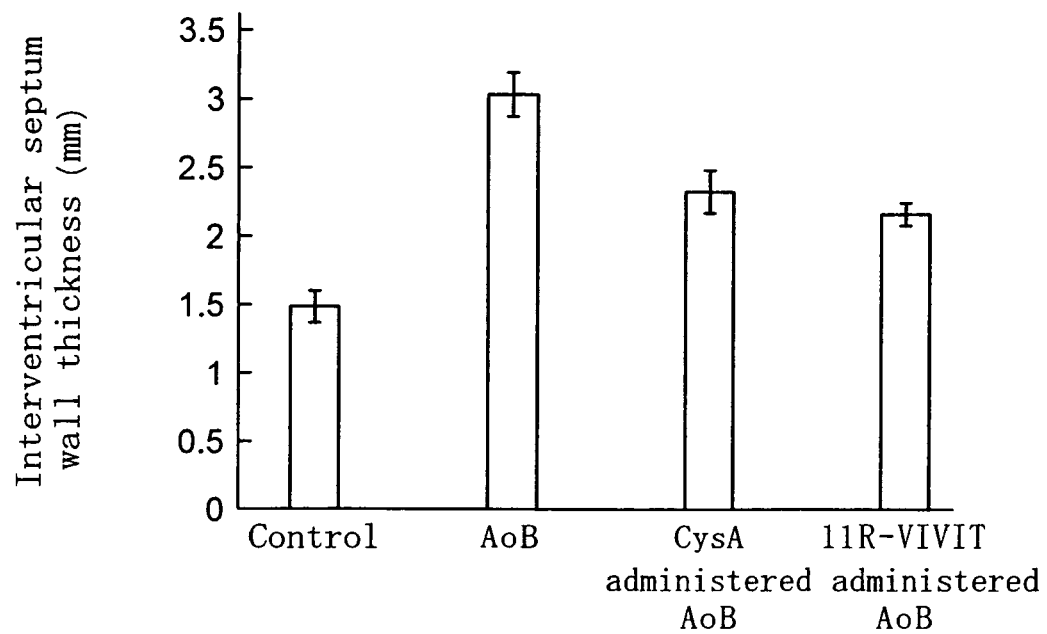
FIG. 9(a) is a graph showing the interventricular septum wall thickness of control, AoB, CysA administered AoB and IIR-VIVIT administered AoB.
Figure 9B:
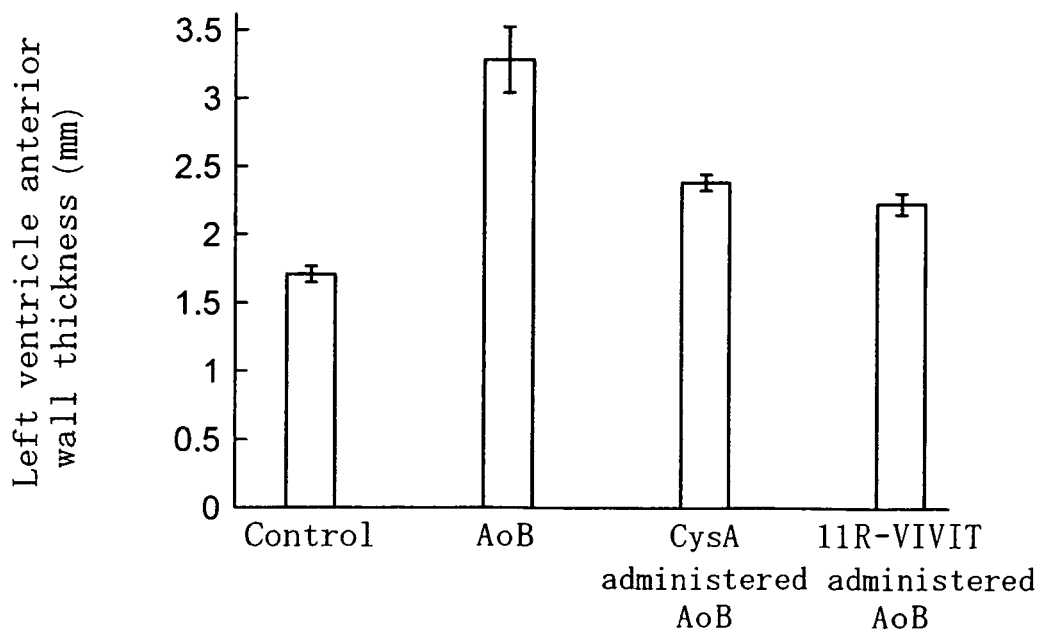
FIG. 9(b) is a graph showing the left ventricle anterior wall thickness of control, AoB, CysA administered AoB and IIR-VIVIT administered AoB.

ULC was conducted by analyzing the thickness of the interventricular septum and left ventricle anterior wall of the rat by ultrasonic echo (made by Hitachi, Ltd.) using a pediatric probe. The results are shown in FIGS. 9(a) and 9(b). As a result, the interventricular septum wall thickness and the left ventricle anterior wall thickness of AoB were both found to improve by administration of 11R-VIVIT.

Figure 10:
FIG. 10 is a microscope image of a tissue specimen of a rat heart.
Figure 10:
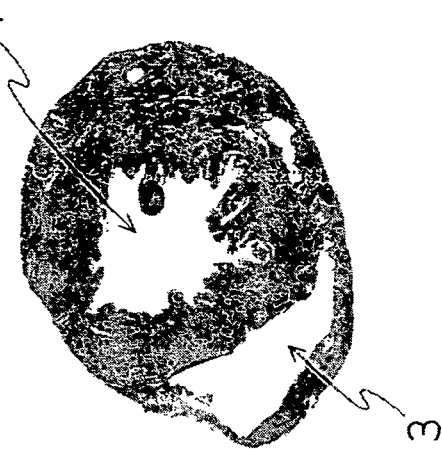
Figure 10:
Figure 10:

The tissue specimen was prepared by surgically removing the rat heart, preparing a section of 5 μm thickness by frozen microtome and staining the obtained section by hematoxylin-eosin staining. The obtained tissue specimen was observed with a microscope (FIG. 10(d)). In FIG. 10, 3 represents the left ventricle and 4 represents the right ventricle. As a result, the symptoms were found to be improved to conditions close to normal by administration of 11R-VIVIT.

Figure 11A:
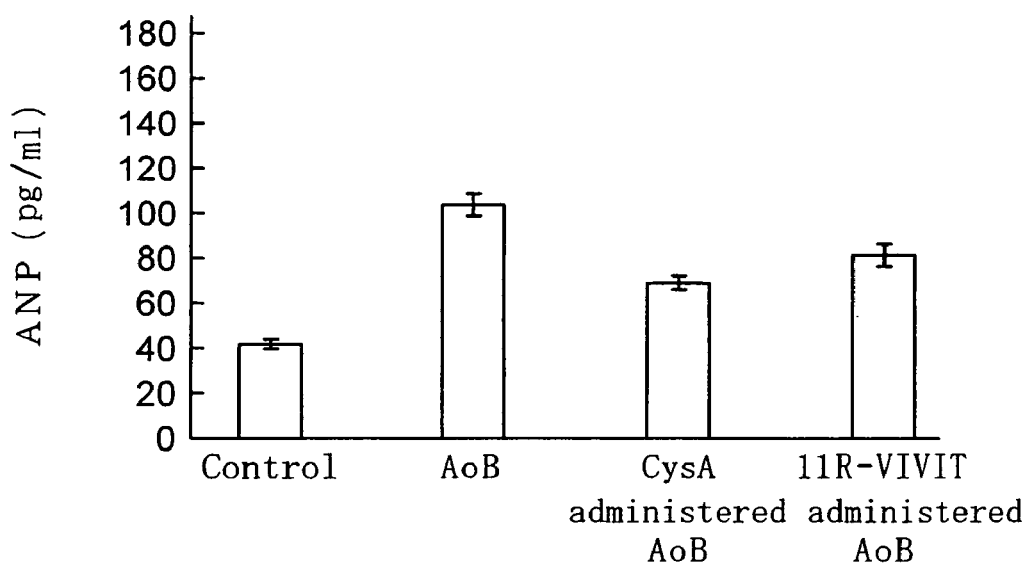
FIG. 11(a) is a graph showing ANP of control, AoB, CysA administered AoB and IIR-VIVIT administered AoB.
Figure 11B:
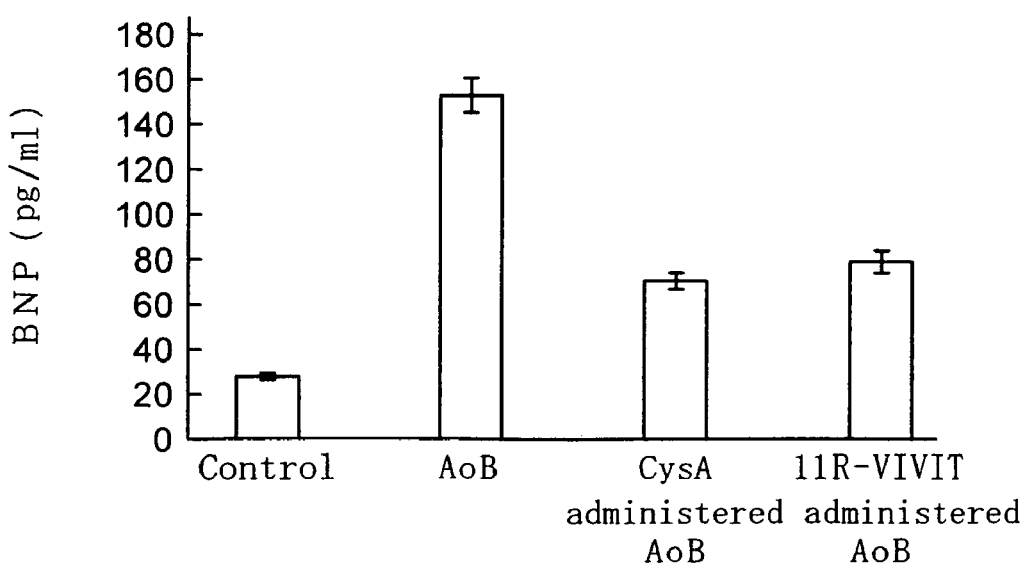
FIG. 11(b) is a graph showing BNP of control, AoB, CysA administered AoB and IIR-VIVIT administered AoB.

Measurement of atrial natriuretic peptide (ANP) and B-type natriuretic peptide (BNP) was commissioned to SRL, Inc. The results are shown in FIGS. 11(a) and 11(b). As a result, the value of ANP and BNP in AoB were found to improve by administration of 11R-VIVIT.

COMPARATIVE EXAMPLE 10

Measurement of ULC, preparation of tissue specimen and blood test was conducted in the same manner as in Example 11, except that AoB to which 11R-VIVIT was not administered was used. The results are shown in FIGS. 9(a), 9(b), 10(b), 11(a) and 11(b).

COMPARATIVE EXAMPLE 11

The effect of CysA to cardiac hypertrophy was studied in the same manner as in Example 11, except that 5 mg/kg of CysA was used instead of 11R-VIVIT. The results are shown in FIGS. 9(a), 9(b), 10(c), 11(a) and 11(b).

TEST EXAMPLE 1

The toxicity of 11R-VIVIT to hepatic function and renal function was studied using 11R-VIVIT administered AoB.

AoB was hypodermically injected every other day for 4 weeks with 0.5 ml of Ringer solution in which 1.5 mg/kg of 11R-VIVIT was dissolved (n=6). Measurement of the following for the obtained AoB was commissioned to SRL, Inc.

As the hepatic function test, glutamate oxaloacetate transaminase (GOT) and glutamate pyruvate transaminase (GPT) were measured and as the renal function test, creatinine (Cr) and urea nitrogen (BUN) were measured. A normal rat and AoB to which 11R-VIVIT was not administered were used as control. The results are shown in Table 1.

TABLE 1

|  | Control | AoB | 11R-VIVIT administered AoB |
|---|---|---|---|
| GOT (IU/l) | 81.2 ± 4.35 | 94.2 ± 14.9 | 99.2 ± 6.24 |
| GPT (IU/l) | 49.6 ± 2.42 | 63.1 ± 14.6 | 55.8 ± 9.95 |
| BUN (mg/dl) | 16.3 ± 1.13 | 21.5 ± 1.38 | 16.6 ± 2.71 |
| Cr (mg/dl) | 0.27 ± 0.02 | 0.37 ± 0.03 | 0.28 ± 0.02 |

The measurement results suggest that the peptide compound of the present invention does not affect the functions of the liver and kidney.

INDUSTRIAL APPLICABILITY

The peptide compound of the present invention can be used as a therapeutic agent for diseases caused by activation of NFAT having extremely few side effects. Specifically, the peptide compound is extremely useful, as the compound can be used for example, as an immunosuppressive agent and a cardiac hypertrophy suppressive agent.

Sequence Listing Free Text

SEQ ID NO. 2: fused peptide sequence
SEQ ID NO. 4: fused peptide sequence

What is claimed is:

1. A therapeutic method, comprising the step of:
   administering a peptide compound comprising 9 to 13 residues of arginine and the amino acid sequence of SEQ ID NO: 1, to a patient at a level that produces immunosuppression in the patient.

2. The therapeutic method of claim 1, wherein said peptide compound comprises 11 residues of arginine.

3. The therapeutic method of claim 1, wherein the compound is administered at a dosage in the range of 1 to 10 mg/kg.

4. The therapeutic method of claim 2, wherein the compound is administered at a dosage in the range of 1 to 10 mg/kg.

5. A therapeutic method, comprising the step of:
   administering a peptide compound comprising 9 to 13 residues of arginine and the amino acid sequence of SEQ ID NO: 1, to a patient at a level that suppresses cardiac hypertrophy in the patient.

6. The therapeutic method of claim 1, wherein said peptide comprises 11 residues of arginine.

7. The therapeutic method of claim 5, wherein the compound is administered at a dosage in the range of 0.1 to 2 mg/kg.

8. The therapeutic method of claim 6, wherein the compound is administered at a dosage in the range of 0.1 to 2 mg/kg.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: human
<220> FEATURE:
```

```
<400> SEQUENCE: 1

Met Ala Gly Pro His Pro Val Ile Val Ile Thr Gly Pro His Glu Glu
 1               5                  10                  15

<210> SEQ ID NO 2
<211> LENGTH: 30
<212> TYPE: PRT
<213> ORGANISM: Artificial Sequence
<220> FEATURE:
<223> OTHER INFORMATION: Description of Artificial Sequence: fusion
      peptide sequence

<400> SEQUENCE: 2

Arg Arg Arg Arg Arg Arg Arg Arg Arg Arg Gly Gly Gly Met Ala
 1               5                  10                  15

Gly Pro His Pro Val Ile Val Ile Thr Gly Pro His Glu Glu
            20                  25                  30

<210> SEQ ID NO 3
<211> LENGTH: 16
<212> TYPE: PRT
<213> ORGANISM: human
<220> FEATURE:

<400> SEQUENCE: 3

Met Ala Gly Pro Pro His Ile Val Glu Glu Thr Gly Pro His Val Ile
 1               5                  10                  15

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: fusion
      peptide sequence

<400> SEQUENCE: 4

Arg Arg Arg Arg Arg Arg Arg Arg Arg Arg Gly Gly Gly Met Ala
 1               5                  10                  15

Gly Pro Pro His Ile Val Glu Glu Thr Gly Pro His Val Ile
            20                  25                  30

<210> SEQ ID NO 5
<211> LENGTH: 20
<212> TYPE: DNA
<213> ORGANISM: human
<220> FEATURE:

<400> SEQUENCE: 5
ctgaccaggg tcctattcca                                              20

<210> SEQ ID NO 6
<211> LENGTH: 20
<212> TYPE: DNA
<213> ORGANISM: human
<220> FEATURE:

<400> SEQUENCE: 6
tggttatccc aagcaagagg                                              20
```